(12) United States Patent
Matsumura et al.

(10) Patent No.: US 7,521,227 B2
(45) Date of Patent: Apr. 21, 2009

(54) CELL OBSERVATION CHAMBER

(75) Inventors: Kazuyuki Matsumura, Tokyo (JP);
Shiro Kanegasaki, Tokyo (JP)

(73) Assignees: Hirata Corporation (JP); ECI, Inc. (JP)

( * ) Notice: Subject to any disclaimer, the term of this patent is extended or adjusted under 35 U.S.C. 154(b) by 172 days.

(21) Appl. No.: 10/572,746

(22) PCT Filed: Sep. 13, 2004

(86) PCT No.: PCT/JP2004/013297

§ 371 (c)(1),
(2), (4) Date: Mar. 21, 2006

(87) PCT Pub. No.: WO2005/028611

PCT Pub. Date: Mar. 31, 2005

(65) Prior Publication Data

US 2007/0065950 A1    Mar. 22, 2007

(30) Foreign Application Priority Data

Sep. 22, 2003   (JP)   ............................. 2003-330735

(51) Int. Cl.
*C12M 3/00*   (2006.01)
(52) U.S. Cl. .................................. 435/288.5
(58) Field of Classification Search ............... 435/288.5
See application file for complete search history.

(56) References Cited

U.S. PATENT DOCUMENTS 7,259,008 B2 *   8/2007   Kanegasaki et al. ...... 435/288.5

FOREIGN PATENT DOCUMENTS

JP   2002-159287   *   6/2002

JP   WO0246356   *   6/2002

OTHER PUBLICATIONS

Kanegasaki, S. ;Momura, Y.; Nitta, N.; Akiyama, S.; Tamatani, T.; Goshoh, Y.; Yoshida, T.; Sato, T.; Kikuchi, Y. "A novel optical assay system for the quantitative measurement of chemotaxis." Journal of Immunlogical Methods, 2003, 282, pp. 1-11.*

* cited by examiner

*Primary Examiner*—Walter D Griffin
*Assistant Examiner*—Bobby Ramdhanie
(74) *Attorney, Agent, or Firm*—Bacon & Thomas, PLLC

(57) ABSTRACT

A biological cell observing chamber (30), wherein an intermediate support body (32) forming a skeleton outer shell structural part is mounted on a bottom support body (31) and a cover block body (33) is mounted on the bottom support body (31) on which the intermediate support body (32) is mounted by using lever mechanisms (36) and (37) incorporating a cam mechanism and a clamp mechanism so that the contact faces thereof can be pressed against each other in the vertical direction. The cam mechanism comprises cam grooves (36b) and (37b) formed in both leg part inner surfaces of U-shaped levers (36) and (37) rotatably supported on the bottom support body (31) and pins (40) and (41) slidably moving in the cam grooves and built in the outer peripheral surfaces of the intermediate support body (32) and the cover block body (33) at corresponding two points. Thus, in the biological cell observing chamber used for the detection of cell chemotaxis and chemotactic cell separator, the assembly and disassembly operations for the intermediate support body forming the skeleton outer shell structural part and the cover block body can be facilitated, and the operability of the chamber can be increased.

5 Claims, 9 Drawing Sheets

Fig.16(1) PRIOR ART
Fig.16(2) PRIOR ART
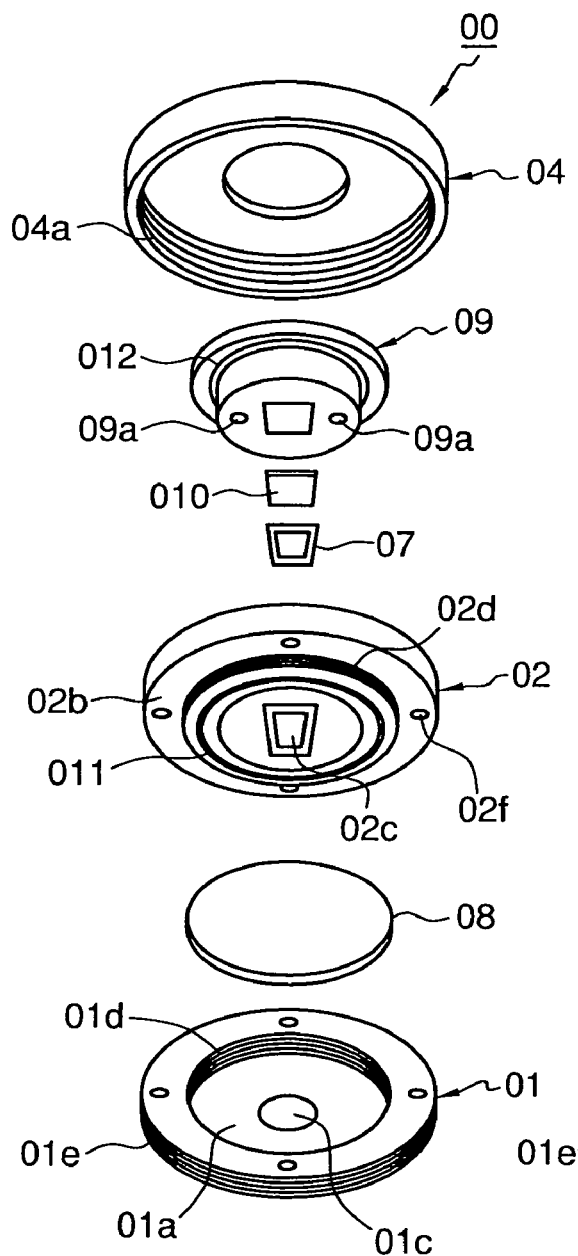
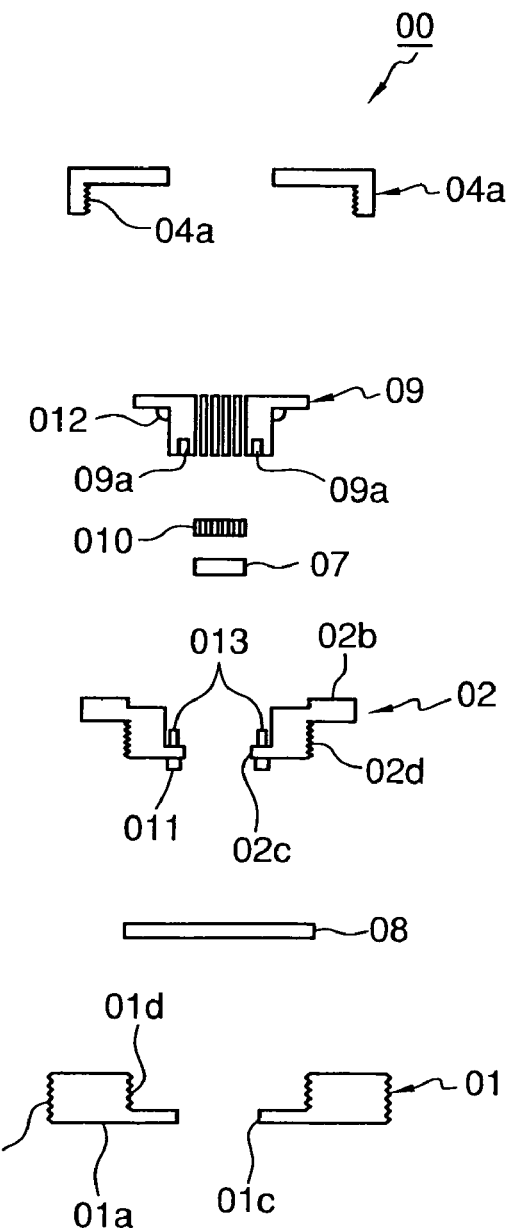

CELL OBSERVATION CHAMBER

BACKGROUND OF THE INVENTION

1. Field of the Invention

The present invention relates to a cell observation chamber, and specifically to a cell observation chamber comprising a plurality of wells for keeping cells, a flow path for cells, and a window for observing the movement of cells to function as the heart of an apparatus used for: for example, determining whether or not cells move in a certain direction by themselves; observing a state where cells move in a certain direction by themselves; measuring the number of cells that have moved in a certain direction by themselves; and isolating cells that move in a certain direction by themselves, that is, an apparatus for detecting cell chemotaxis and for isolating chemotactic cells.

2. Description of the Prior Art

There have conventionally been proposed and marketed various kinds of apparatuses for detecting cell chemotaxis and for isolating chemotactic cells. In particular, there has been proposed an apparatus, as described in Japanese Patent Laid-Open Publication No. 2002-159287, adapted to be capable of observing and quantitating the self-based movement of cells precisely and easily using a few cell samples to detect the chemotaxis of the cells due to chemotactic factor or the chemotaxis inhibition of the cells due to chemotactic factor inhibitor. In this apparatus, it is also possible to isolate the cells utilizing the chemotaxis of the cells.

In the apparatus for detecting cell chemotaxis and for isolating chemotactic cells described in the foregoing publication, a cell observation chamber is arranged as follows.

As shown in FIG. 16, the cell observation chamber 00 comprises: a circular shallow dish-shaped bottom support body 01 with a window 01c for observing the movement of cells provided in the center of the bottom part thereof; a glass substrate 08 adapted to be placed on the bottom part 01a of the bottom support body 01; a dish-shaped intermediate support body 02 adapted to be attached to the bottom support body 01 to press and fix the glass substrate 08 from above onto the bottom part 01a by connecting a cover 04 to be described hereinafter to the bottom support body 01 with screws; a substrate 07 and a packing member 010 adapted to be fitted into a rectangular opening portion 02c that is formed in the center of the bottom part of the intermediate support body 02 to be fixed onto the glass substrate 08; a block body 09 adapted to be fitted into the central recessed portion of the intermediate support body 02 to press and fix the substrate 07 onto the glass substrate 08 through the packing member 010 using pressing screws not shown in the figure; and a cover 04 adapted to be attached to the bottom support body 01 through a screw connection to press and fix the block body 09 from above. The substrate 07 is made of silicon single-crystal material.

The connection between the bottom support body 01 and the intermediate support body 02 is to be made by screwing a male thread 02d formed in the outer peripheral surface of the body part of the intermediate support body 02 into a female thread 01d formed in the inner peripheral surface of the body part of the bottom support body 01 and by a screw connection between the bottom support body 01 and the cover 04. The screw connection between the bottom support body 01 and the cover 04 is to be made by screwing a male thread 01e formed in the outer peripheral surface of the bottom support body 01 into a female thread 04a formed in the inner peripheral surface of the sleeve part of the cover 04. The intermediate support body 02 is to be positioned on the bottom support body 01 by inserting guide pins (not shown in the figure) disposed on the upper surface of the body part of the bottom support body 01 into guide pin receiving holes 02f formed in the lower surface of the flange part 02b of the intermediate support body 02. Also, the block body 09 is to be positioned in the intermediate support body 02 by inserting guide pins 013 disposed on the bottom surface of the intermediate support body 02 into guide pin receiving holes 09a formed in the bottom surface of the block body 09.

Then, in a state where the above components are assembled integrally and used, at least a pair of wells and a flow path for communicating of these wells are to be formed between the substrate 07 and the glass substrate 08. One of these wells is to be provided with cell suspension, while the other thereof is to be provided with chemotactic factor containing solution, so that cells move from one to the other of the wells through the flow path in response to the chemotactic factor. A microscopic observation is to be carried out through the window 01c to observe the state and to measure the number of moving cells.

The injection of cell suspension and chemotactic factor containing solution into one and the other wells that are formed between the substrate 07 and the glass substrate 08 is to be performed using a micropipette through specialized through holes formed, respectively, in the block body 09, the packing member 010, and the substrate 07. After assembling the bottom support body 01, the intermediate support body 02, and the cover 04, an O-ring 011 is to be interposed between the intermediate support body 02 and the glass substrate 08 so that no solution filling the bottom support body 01 leaks. On the other hand, the packing member 010 is also provided between the substrate 07 and the block body 09 so as to be useful in preventing each solution from leaking from the wells and the flow path for communicating of the wells.

Since the conventional cell observation chamber is arranged as mentioned above, the attachment of the intermediate support body 02 to the bottom support body 01 and of the cover 04 to the bottom support body 01 are both achieved through a screw connection, which therefore requires a constant pressure to bring the components into pressurized contact with each other and thereby requires a specialized assembling tool, resulting in poor operationality and complication in disassembling and assembling.

Patent Document 1: Japanese Patent Laid-Open Publication No. 2002-159287

Patent Document 2: Japanese Patent Laid-Open Publication No. 2003-088357

SUMMARY OF THE INVENTION

The present invention has been made to solve the above-described problems of the conventional cell observation chamber, and an object thereof is to provide a cell observation chamber that requires no specialized assembling tool for the attachment of an intermediate support body to a bottom support body and of a block body integrated with a cover to the bottom support body with the intermediate support body attached thereto, and adapted to be capable of keeping a constant pressure at any time to bring the associated components into pressurized contact with each other, resulting in a dramatic improvement in operationality in assembling and disassembling.

In accordance with the present invention, the foregoing object can be achieved with the following cell observation chamber.

That is, the cell observation chamber is provided in an apparatus used for detecting cell chemotaxis and for isolating chemotactic cells, the chamber comprising: a dish-shaped bottom support body with a window for observing the movement of cells provided in the center of the bottom part thereof; a glass substrate adapted to be placed on the bottom surface of the bottom support body; a dish-shaped intermediate support body with an opening portion formed in the center of the bottom part thereof, the intermediate support body being adapted to be attached to the bottom support body to press and fix the glass substrate from above onto the bottom surface of the bottom support body; a substrate with a plurality of through holes for guiding cell suspension and chemotactic factor containing solution therethrough formed therein in a vertically penetrating manner, the substrate being adapted to be fixed onto the surface in the central part of the glass substrate, in which a concavo-convex shape is formed in the surface facing the glass substrate to form at least a pair of wells and a flow path for communicating of the wells with the glass substrate; a packing member with a plurality of through holes for guiding the cell suspension and the chemotactic factor containing solution therethrough formed therein in a vertically penetrating manner, the packing member being adapted to be fitted into the opening portion that is formed in the center of the bottom part of the intermediate support body to press the substrate from above; and a dish-shaped cover block body with a plurality of through holes for guiding the cell suspension and the chemotactic factor containing solution therethrough formed in the center of the bottom part thereof in a vertically penetrating manner, the cover block body being adapted to be attached to the bottom support body with the intermediate support body attached thereto to press and fix the substrate from above onto the glass substrate through the packing member, wherein one of the pair of wells is adapted to be provided or given with the cell suspension through each one of the plurality of through holes that are formed, respectively, in the cover block body, the packing member, and the substrate, while the other of the wells is adapted to be provided or given with the chemotactic factor containing solution through each one of the plurality of through holes that are formed, respectively, in the cover block body, the packing member, and the substrate, so that a state where cells move from one to the other of the wells through the flow path is observed and the number of the cells is measured through the window provided in the bottom support body, and wherein the attachment of the intermediate support body and of the cover block body to the bottom support body is achieved by bringing the respective contact surfaces into vertically pressurized contact with each other using lever mechanisms or clamp mechanisms with a cam mechanism incorporated therein.

In accordance with the cell observation chamber, the attachment of the intermediate support body to the bottom support body and of the cover block body to the bottom support body is achieved by bringing the respective contact surfaces into vertically pressurized contact with each other using (a pair of) lever mechanisms or clamp mechanisms with the cam mechanism incorporated therein, which eliminates the need for a specialized tool for assembling and disassembling, whereby it is possible to improve the operationality in assembling and disassembling dramatically. This also makes it possible to keep a constant pressure at any time to bring the components associated with the attachment into pressurized contact with each other, whereby it is possible to prevent the solution in the chamber from leaking reliably.

In a preferred embodiment, the cam mechanism comprises: cam grooves formed, respectively, in both leg parts of two U-shaped levers that are supported rotatably by the bottom support body; and pins implanted, respectively, at two corresponding points on the outer peripheral surface of the intermediate support body and the cover block body, the pins being adapted to move within the cam grooves in a sliding manner. This allows the structure of the cam mechanism to be simplified significantly, and the attachment/detachment of the intermediate support body to/from the bottom support body and of the cover block body to/from the bottom support body can be achieved only by rotating the respective U-shaped levers, which facilitates the operation of the cam mechanism significantly.

In another preferred embodiment, a guide block body is further attached to the cover block body, in the guide block body being formed a plurality of through holes for guiding a micropipette that has inhaled either the cell suspension or the chemotactic factor containing solution therethrough in a vertically penetrating manner. This facilitates significantly the operation of injecting or removing the cell suspension into/from one of the wells in the cell observation chamber using the micropipette and the operation of injecting or removing the chemotactic factor containing solution into/from the other of the wells in the cell observation chamber using the micropipette.

As described heretofore, in accordance with the present invention, the attachment of the intermediate support body to the bottom support body and of the cover block body to the bottom support body is achieved by bringing the respective contact surfaces into vertically pressurized contact with each other using the lever mechanisms or the clamp mechanisms with the cam mechanism incorporated therein, which eliminates the need for a specialized tool for assembling and disassembling, whereby it is possible to improve the operationality in assembling and disassembling dramatically. This also makes it possible to keep a constant pressure at any time to bring the components associated with the attachment into pressurized contact with each other, whereby it is possible to prevent the solution in the chamber from leaking reliably.

Also, in the case of further attaching the guide block body with a plurality of through holes for guiding the micropipette therethrough formed therein in a penetrating manner to the cover block body, the operation of injecting or removing cell suspension and chemotactic factor containing solution into/from the wells using the micropipette can be facilitated significantly.

BRIEF DESCRIPTION OF THE DRAWINGS

FIGS. 16(1) and 16(2) are exploded views of a conventional cell observation chamber.

DESCRIPTION OF THE PREFERRED EMBODIMENTS

It is arranged that the attachment of an intermediate support body to a bottom support body and of a cover block body to the bottom support body for constituting a cell observation chamber is achieved by bringing the respective contact surfaces into vertically pressurized contact with each other using lever mechanisms or clamp mechanisms with a cam mechanism incorporated therein. In this case, it is arranged that the cam mechanism comprises: cam grooves formed, respectively, in both leg parts of two U-shaped levers that are supported rotatably by the bottom support body; and pins implanted, respectively, at two corresponding points on the outer peripheral surface of the intermediate support body and the cover block body, the pins being adapted to move within the cam grooves in a sliding manner, and that there are provided specialized cam mechanisms, respectively, for the attachment of the intermediate support body to the bottom support body and of the cover block body to the bottom support body. It is also preferable that a guide block body for making it easy to get the needlepoint of a micropipette in and out be attached to the cover block body.

Next will be described an embodiment of the present invention.

The principle of the operation of a chamber in an apparatus for detecting cell chemotaxis and for isolating chemotactic cells to which the present invention is applied will first be described. In this chamber, a plurality of wells are connected and communicate with each other through a flow path, in each well being provided two pipes: one is for injecting or removing samples, and the other is for preventing the pressure in the well from increasing or decreasing due to the operation of injecting or removing the samples. These pipes may be formed by through holes formed in a block. It is here noted that the flow path is a part for communicating of two wells, that is, a channel through which cells pass when moving from one to the other of the wells. In accordance with the apparatus, since the liquid flow toward the opposite wells in the flow path is unlikely to occur when injecting or removing samples, there is no possibility that the liquid in the wells provided on both ends of the flow path intermingles with each other, whereby it is possible to detect the case where cells mainly move based only on the effect of chemotactic factor.

Figure 1:
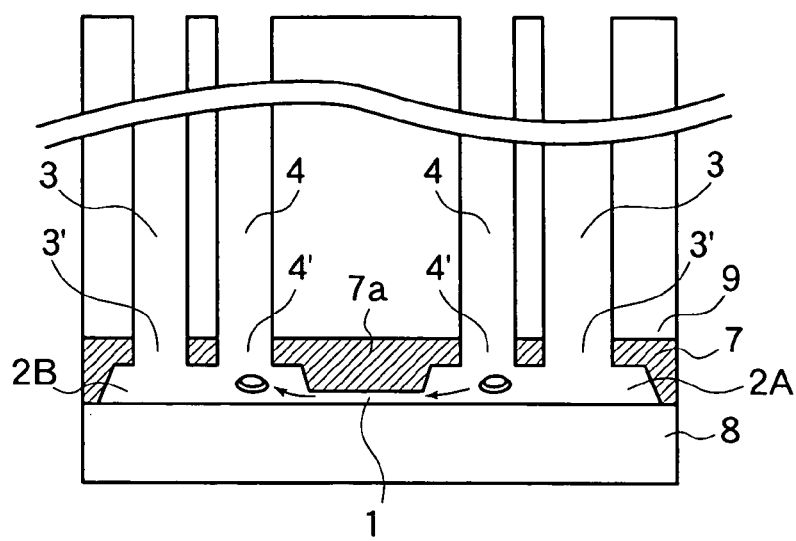
FIG. 1 is a schematic diagram, partially in cross-section, of an embodiment of the cell observation chamber of the present invention illustrating the flow path of cells between the wells of the chamber.
Figure 2:
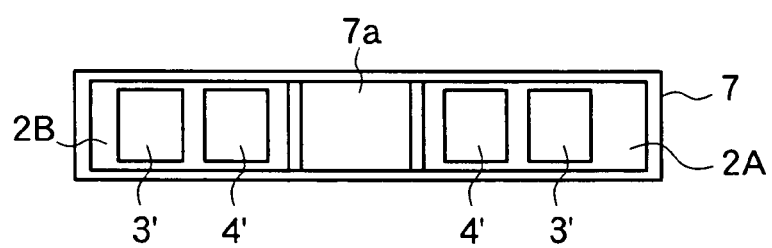
FIG. 2 is a top plan view of the cell observation chamber of FIG. 1.

To describe the principle based on the accompanying drawings, in FIGS. 1 and 2, the numeral 1 indicates a flow path, and the numeral 2 indicates wells for storing samples such as cell suspension and specimen solution, consisting of a pair of wells 2A and 2B. These samples are provided or removed to/from the wells 2 through the through holes 3 formed in the block body 9 using a micropipette, etc. When one well 2A of the wells 2 is provided with the cell suspension, cells try to move toward the other well 2B and pass through the flow path 1 if the specimen solution put in the well 2B contains chemotactic factor (chemotactic factor containing solution).

When providing the cell suspension, one sample, to the well 2A through the through hole 3 using a micropipette, etc., there is a possibility that cells move toward the well 2B provided on the opposite side through the flow path 1 due to the pressure of the liquid injected. This situation, if occurred, causes confusion about determining whether or not the movement of the cells is due to the chemotactic factor contained in the specimen, and in the case of aiming at isolating cells, causes desired cells to intermingle with other cells, which makes it impossible to achieve the purpose. In order to solve the problem, this apparatus is arranged in such a manner that an injection pressure to be applied to the through hole 3 is released toward the through hole 4 to prevent cells from being flowed forcibly toward the flow path 1.

Also, when providing the specimen solution to the well 2B through the through hole 3 using a micropipette, etc., there is a possibility that the specimen solution enters the well 2A provided on the opposite side through the flow path 1 due to the pressure of the liquid injected to intermingle with the cell suspension, and therefore the phenomenon that cells pass through the flow path 1 due to the chemotaxis thereof may be confused or disturbed. In order to prevent such a situation from occurring, a through hole 4 is also provided in the well 2B for storing the specimen.

Thus providing the through holes 4 that communicate with the through holes 3 for injecting the samples therethrough can minimize the horizontal impact of the liquid pressure and thereby can determine whether or not the specimen solution has chemotaxis more precisely. The effect of reducing pressure difference using the through holes 4 is also effective in reducing pressure reduction when removing samples such as cells from the wells, which therefore makes it easy to remove the samples.

To describe the case of injecting samples into the wells 2 in this apparatus with reference to FIG. 1, the wells 2A and 2B and the flow path 1 are preliminarily filled with cell isotonic solution, and then approximately the same quantity of cell suspension and chemotactic factor containing solution is injected, respectively, through the through hole 3 of the well 2A and the through hole 3 of the well 2B. This allows the pressure increase when injecting the samples to be reduced by the through holes 4.

Figure 3:
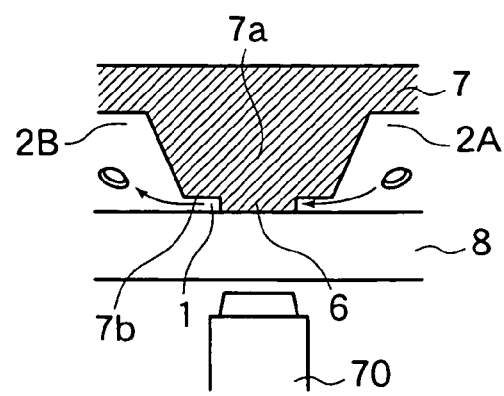
FIG. 3 is a partial, enlarged schematic view, partially in cross-section, of the cell observation chamber of FIG. 1 showing the cell flow path.
Figure 4:
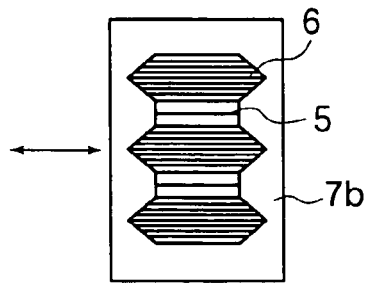
FIG. 4 is a bottom plan view of the substrate 7 of the cell observation chamber of FIG. 1.
Figure 5:
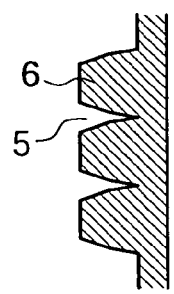
FIG. 5 is a side, cross-sectional view of the substrate 7 of the cell observation chamber of FIG. 1.

As shown in FIGS. 3 to 5, the flow path 1 is composed of one or a plurality of, for example about 100, grooves 5 formed in a barrier 6 along the direction or the opposite direction from the well 2A toward the well 2B, the barrier 6 running in the direction perpendicular to the direction or the opposite direction from the well 2A toward the well 2B. These grooves 5 are formed at a width in accordance with the diameter of cells or the deformability thereof. Thus providing the grooves 5 makes it possible to observe the cells at individual level and also to isolate the cells into desired classes.

It is noted that the numeral 7a in FIGS. 1 to 3 indicates a bank formed between the wells 2A and 2B, while the numeral 7b in FIGS. 3 and 4 indicates a terrace formed on the bank 7a. The terrace 7b is a flat portion surrounding the barrier 6.

An observation of a state where cells move through the flow path 1 and a measurement of the number of cells that currently pass or have passed through the flow path 1 are to be made by setting a sensing device, for example, a microscope 70 in such a manner that the sensing device faces the flow path 1 through a glass substrate 8 as shown in FIG. 3. Also, combining the microscope with a video camera or a CCD camera makes it possible to record the progress of the cell movement automatically.

Defining such an apparatus as mentioned above, in which the wells 2A and 2B with the through holes 3 and 4 provided respectively therein are communicated with each other through the flow path 1, as one unit and integrating a plurality of units makes it possible to construct an apparatus whereby the movement (chemotaxis) of cells can be detected and chemotactic cells can be isolated at the same time for other kinds of specimens or other kinds of cells. Since the size of such an apparatus is wholly reduced, it is possible to treat samples at a small quantity. In addition, the treatment can be automated easily with a program control system for the injection/removal quantity of the liquid.

Such a unit as mentioned above, in which the wells 2A and 2B with the through holes 3 and 4 provided respectively therein are communicated with each other through the flow path 1, is actually manufactured as follows.

The inner shape of the wells 2A and 2B and the flow path 1 can be formed by applying a known technique for manufacturing an integrated circuit onto the surface of a substrate 7 made of silicon single-crystal material. Arranging the substrate 7 with a concavo-convex shape obtained by thus transferring the inner shape of the wells 2A and 2B and the flow path 1 thereto engraved on the surface thereof to face and overlap the glass substrate 8 causes the wells 2A and 2B and the flow path 1 to be formed between the substrates 7 and 8.

In the substrate 7, through holes 3' for guiding cell suspension or chemotactic factor containing solution therethrough are also formed correspondingly to the respective wells 2A and 2B in a vertically penetrating manner, and through holes 4' for reducing pressure increase or pressure reduction that occurs when injecting or removing the solutions into/from the wells 2A and 2B are formed in pairs with the respective through holes 3' in a vertically penetrating manner. These pairs of through holes 3' and 4' are communicated with each other through the well 2A or 2B and communicate with the respective through holes 3 and 4 that are formed in the block body 9 in a vertically penetrating manner. It is noted that there is actually interposed a packing between the substrate 7 and the block body 9 so as to seal the liquid therebetween.

Next will be described in detail the cell observation chamber according to the present embodiment in which a plurality of such units as mentioned above, in which the wells 2A and 2B with the through holes 3 and 4 provided respectively therein are communicated with each other through the flow path 1, are incorporated.

The outline of the overall structure of the apparatus for detecting cell chemotaxis and for isolating chemotactic cells to which the cell observation chamber according to the present embodiment is applied will first be described.

Figure 6:
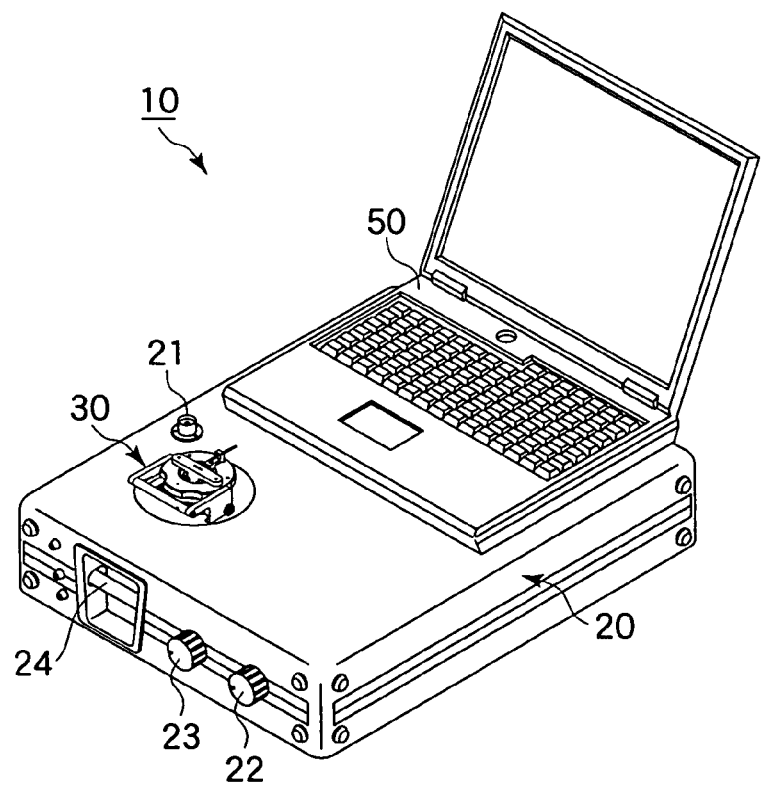
FIG. 6 is a perspective view of an apparatus for detecting cell chemotaxis and for isolating chemotactic cells, utilizing a cell observation chamber of the present invention.
Figure 7:
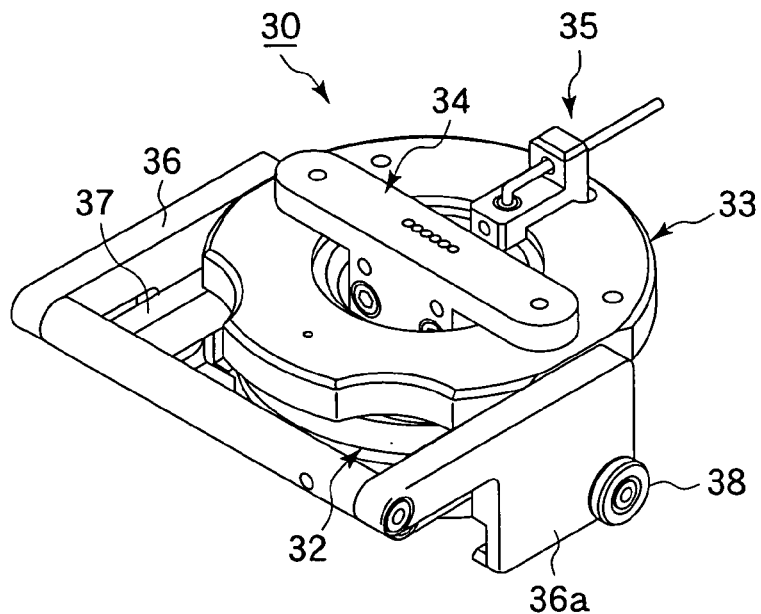
FIG. 7 is a perspective view of the cell observation chamber of FIG. 1.

As shown in FIG. 6, in the apparatus 10 for detecting cell chemotaxis and for isolating chemotactic cells to which the cell observation chamber 30 according to the present embodiment is applied, the cell observation chamber 30 is housed in such a manner as to be partially exposed on the upper surface of a relatively low casing 20 having a rectangular parallelepiped shape. Also, a laptop computer 50 is placed on the upper surface of the casing 20, and the laptop computer 50 is adapted to operate to, for example, give instructions to a temperature control section for solutions containing cell suspension, etc. and analyze, record, and monitor temperature data and/or cell observation data. The monitoring includes displaying an image of an actual cell movement.

Since a level 21 is additionally attached to the upper surface of the casing 20, it is possible to monitor the evenness of the apparatus 10 constantly. Further, a brightness (light intensity) adjustment knob 22 for a cell observation image in the microscope, a position adjustment knob 23 for the microscope, and a focal point adjustment lever 24, etc. are attached to the front surface of the casing 20 in this order from the lower right to the upper left in FIG. 6. Since an optical axis, not shown in the figure, in the optical system of the microscope is arranged horizontally in the casing 20, it is possible to reduce the height of the casing 20 and therefore the apparatus 10, which makes it possible to perform the operation of detecting cell chemotaxis, isolating chemotactic cells, and measuring the number of cells in a sitting posture using the apparatus 10 placed on a desk, resulting in a significant improvement in operationality.

The cell observation chamber 30 is arranged as follows.

As shown in FIGS. 7 to 10, 13, and 14, the arrangement of the cell observation chamber 30 will be understood as follows based on the appearance thereof and a partially disassembled state achieved by a simple rotational operation of cam control levers 36 and 37 to be described hereinafter. That is, onto a circular dish-shaped bottom support body 31 that is arranged in the lowest part is attached an intermediate support body 32 having also a circular dish shape; onto the intermediate support body 32 is attached a cover block body 33 having also a circular dish shape with the relatively thick bottom part 33a and the relatively wide outer peripheral flange part 33b; onto the cover block body 33 is attached a guide block body 34 across the central recessed portion 33c of the cover block body 33 in such a manner that the central enlarged portion 34a thereof is sunk into the central recessed portion 33c; and on the upper surface of the cover block body 33 is seated a pedestal part 35a of a temperature sensor 35.

Then, rotating the cam control lever 36 causes the cover block body 33 to be brought into pressurized contact with the intermediate support body 32 from above, which causes the intermediate support body 32 to be brought into pressurized contact with the bottom support body 31 from above, so that the cover block body 33 is finally to be attached to the bottom support body 31. Also, rotating the cam control lever 37 causes the intermediate support body 32 to be brought into pressurized contact with the bottom support body 31 from above and to be attached thereto. It is noted that in an actual attachment order, the intermediate support body 32 is first attached to the bottom support body 31, and the cover block body 33 is then attached to the bottom support body 31. In the case of a disassembling operation, the operation is to be performed in the reverse order. The cover block body 33 corresponds to one obtained by combining the block body 09 and the cover 04 in the conventional cell observation chamber 00 (refer to FIG. 16).

The cam control levers 36 and 37 each have a U shape when viewed from above, and the end portions 36a and 37a of the both leg parts thereof exist on the outer peripheral surface of the body part 31b of the circular dish-shaped bottom support body 31 to be supported rotatably around a pair of support shafts 38 that are implanted symmetrically with respect to the axial center of the body part. Also, the end portions 36a and 37a of the both leg parts are enlarged into a rectangular shape when viewed from front, in the inner surface of which being formed curved cam grooves 36b and 37b, respectively, for the cam control levers 36 and 37 (refer to FIGS. 13 and 14).

Figure 11:
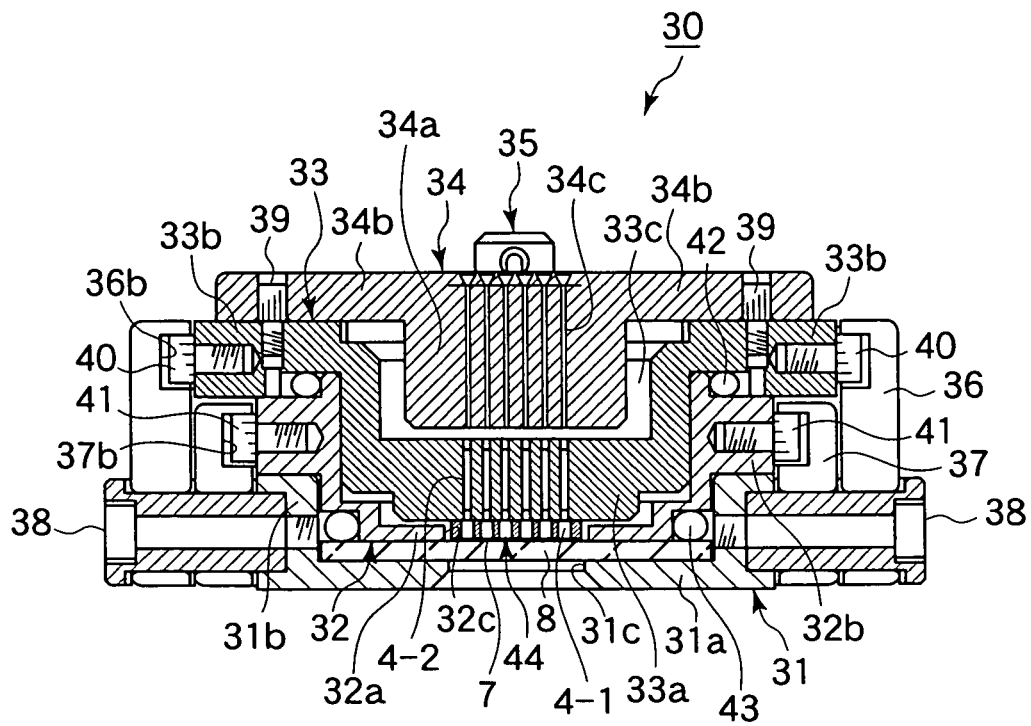
FIG. 11 is a front cross-sectional view of the cell observation chamber of FIG. 1.
Figure 14:
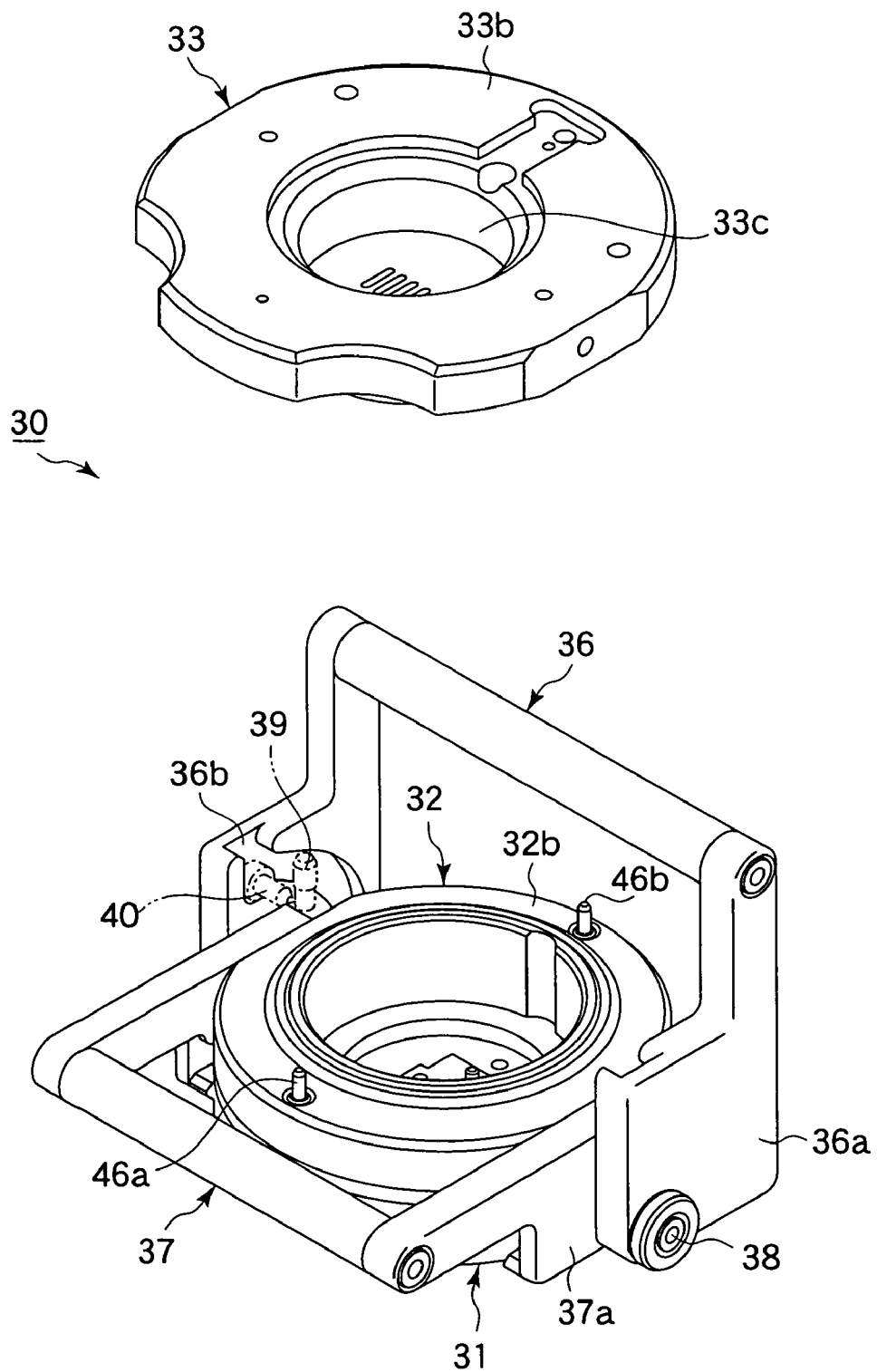
FIG. 14 is a perspective view of the cell observation chamber of FIG. 1, further disassembled by removal of the cover block body 33.

On the outer peripheral surface of the outer peripheral flange part 33b of the circular dish-shaped cover block body 33, there are implanted pins 40 symmetrically with respect to the axial center of the flange part (refer to FIGS. 14 and 11). The pins 40 are fitted into the cam grooves 36b of the cam control lever 36 so as to move within the cam grooves 36b in a sliding manner when the cam control lever 36 is rotated.

This causes the lower surface of the outer peripheral flange part 33b of the cover block body 33 to come close to and to be brought into contact with the upper surface of the outer peripheral flange part 32b of the intermediate support body 32 from above, and finally to be attached to the bottom support body 31 while pressing a packing member 44 and the substrate 7 that are fitted into an opening portion 32c of the intermediate support body 32 against the glass substrate 8. Also, rotating the cam control lever 36 reversely causes the cover block body 33 to be detached from the bottom support body 31. Between the outer peripheral flange part 33b of the cover block body 33 and the outer peripheral flange part 32b of the intermediate support body 32, there is interposed an O-ring 42 for preventing medium from leaking from an inner space to be formed between the cover block body 33 and the intermediate support body 32 when the cover block body 33 is attached to the intermediate support body 32.

Similarly, on the outer peripheral surface of the outer peripheral flange part 32b of the circular dish-shaped intermediate support body 32, there are implanted pins 41 symmetrically with respect to the axial center of the flange part (refer to FIG. 11). The pins 41 are fitted into the cam grooves 37b of the cam control lever 37 so as to move within the cam grooves 37b in a sliding manner when the cam control lever 37 is rotated. This causes the lower surface of the outer peripheral flange part 32b of the intermediate support body 32 to come close to and to be brought into contact with the upper surface of the body part 31b of the bottom support body 31 from above, and to be attached to the bottom support body 31 firmly. Also, rotating the cam control lever 37 reversely causes the intermediate support body 32 to be detached from the bottom support body 31.

In the central enlarged portion 34a of the guide block body 34, there are formed six narrow through holes 34c in a vertically penetrating manner aligned in the longitudinal direction of the guide block body 34. When an operator inserts or withdraws the needlepoint of a micropipette (not shown in the figure) carrying a sample such as cell suspension or specimen solution into/from the chamber 30, these through holes 34c are useful in guiding the needlepoint of the micropipette and in guiding the solution discharged from the micropipette to the well to be described hereinafter (this well is identical with one of the foregoing pair of wells 2A and 2B (FIG. 1)). The position where the six through holes 34c are aligned is displaced slightly toward one side of a centerline "a" dividing the guide block body 34 into two sections in the width direction when viewed from above (refer to FIG. 8).

The guide block body 34 is positioned and attached onto the flange part 33b detachably with pins 39 penetrating through arm parts 34b and 34b on either side of the central enlarged portion 34a and the flange part 33b of the cover block body 33. Therefore, after the guide block body 34 is detached from the cover block body 33 and rotated by 180 degrees so that the positions of the arm parts 34b and 34b on either side are switched with each other, the guide block body 34 can be attached again onto the flange part 33b of the cover block body 33 detachably by being positioned using the pins 39 similarly before the switching. In this case, the position where the six through holes 34c are aligned is symmetrical to the alignment position before the switching with respect to the centerline "a".

In order to position the cover block body 33 and the intermediate support body 32 relatively in the circumferential direction, a pair of positioning pins 46a and 46b penetrate through holes formed respectively therefor across the cover block body 33 and the intermediate support body 32. Similarly, in order to position the intermediate support body 32 and the bottom support body 31 relatively in the circumferential direction, a pair of positioning pins 47a and 47b penetrate through holes formed respectively therefor across the intermediate support body 32 and the bottom support body 31. The pins 46a and 46b and the pins 47a and 47b have their respective different diameters to fulfill a function of preventing an assembling error in an assembling operation from occurring.

Next will be described the internal structure of the cell observation chamber 30 in detail.

In the center of the bottom part 31a of the bottom support body 31, there is provided a window 31c for observing the movement of cells. Also, the transparent glass substrate 8 is placed on the bottom surface of the body. When the intermediate support body 32 is attached to the bottom support body 31, the glass substrate 8 is pressed firmly against and fixed to the bottom part 31a by the bottom part 32a of the intermediate support body 32. Between the bottom part 32a and the glass substrate 8 and on the outer peripheral side thereof, there is interposed an O-ring 43 to prevent medium from leaking from an inner space to be formed therebetween.

The substrate 7 is placed on the surface in the central part of the glass substrate 8. The glass substrate 8 and the substrate 7 are identical with the foregoing glass substrate 8 and substrate 7 in FIG. 1 having basically the same structure. Therefore, on the surface of the substrate 7 facing the glass substrate 8, there are engraved six units of concavo-convex shapes obtained by transferring the inner shape of the pair of wells 2A and 2B and the flow path 1 for communicating of the wells thereto, and in a state where the shapes are arranged to face and overlap the glass substrate 8, six units of combination structures of the wells 2A and 2B and the flow path 1 are formed between the substrates 7 and 8.

In the substrate 7, the through holes 3' for guiding cell suspension or chemotactic factor containing solution therethrough are also formed correspondingly to the respective wells 2A and 2B in a vertically penetrating manner, and the through holes 4' for reducing pressure increase or pressure reduction that occurs when injecting or removing the solutions into/from the wells 2A and 2B are formed in pairs with the respective through holes 3' in a vertically penetrating manner. These pairs of through holes 3' and 4' are communicated with each other through the well 2A or 2B.

The opening portion 32c is formed in the central part of the bottom part 32a of the intermediate support body 32, and the packing member 44 having a thickness slightly greater than that of the bottom part 32a is fitted into the opening portion 32c. When the cover block body 33 is attached to the bottom support body 31 as mentioned above, the packing member 44 protrudes from the opening portion 32c to press the substrate 7 placed on the glass substrate 8 from above against the glass substrate 8.

Figure 12:
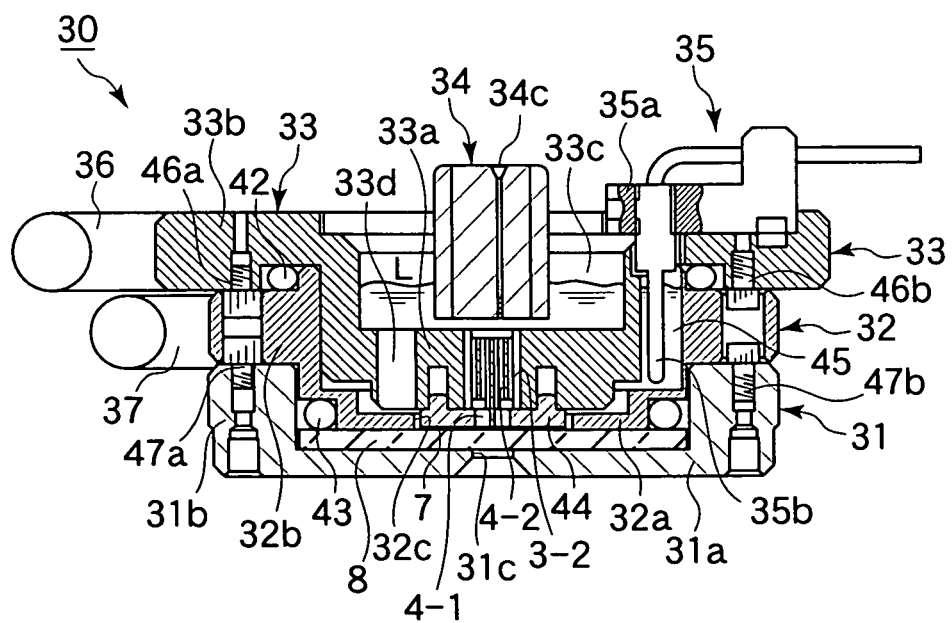
FIG. 12 is a side cross-sectional view of the cell observation chamber of FIG. 1.
Figure 13:
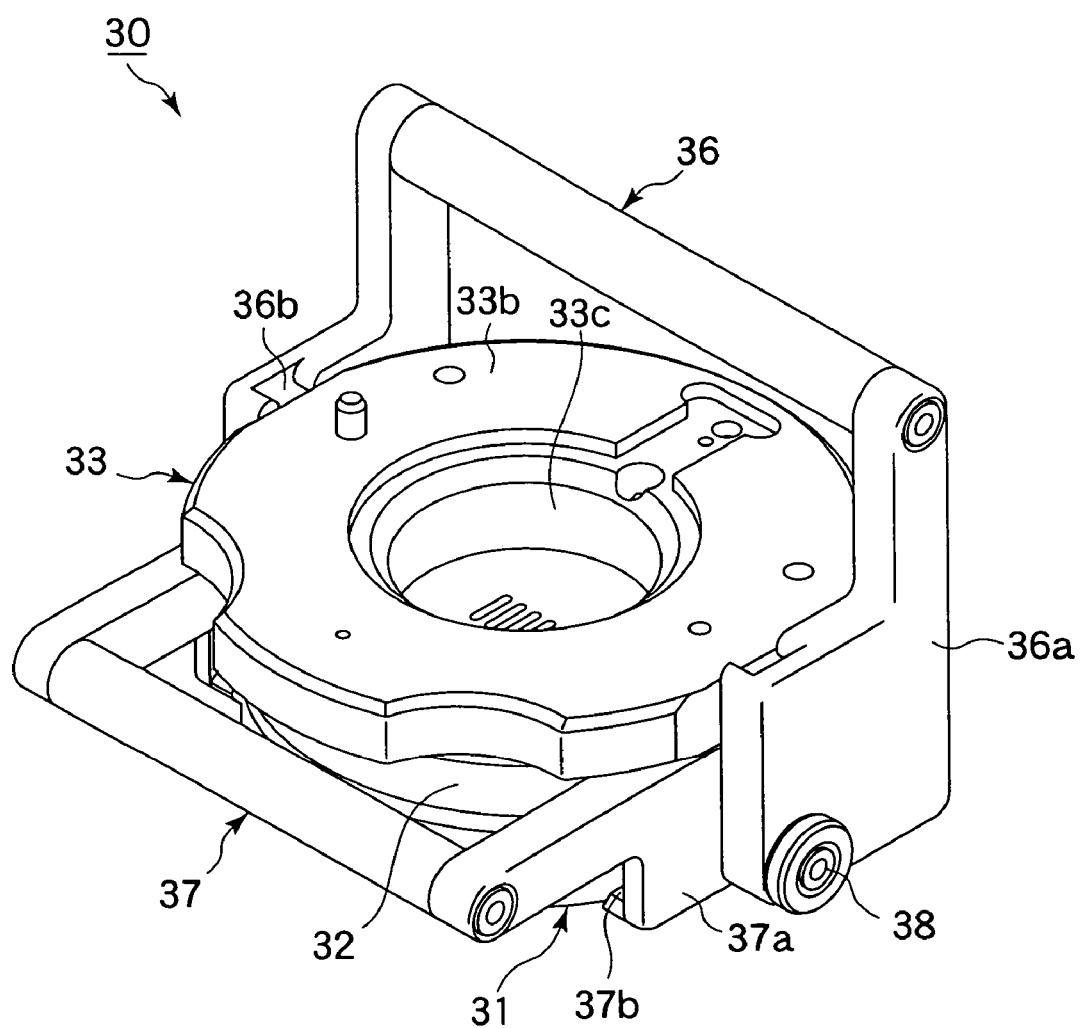
FIG. 13 is a perspective view of the cell observation chamber of FIG. 1, partially disassembled by removal of the guide block body 34.

The substrate 7, which has a very small thickness, is represented as a heavy solid line segment sandwiched between the glass substrate 8 and the packing member 44 in FIGS. 11 and 12. The shape of the through holes 3' and 4', the wells 2A and 2B, and the flow path 1 formed in the substrate 7 is not shown in the figures.

In the packing member 44, there are formed the same number of through holes 3-1 and 4-1 that communicate, respectively, with the through holes 3' and 4' formed in the substrate 7 in a penetrating manner as the total number of the through holes 3' and 4' in a vertically penetrating manner. Since the through holes 3' and 4' are formed in each of the wells 2A and 2B in a pair, a total of four through holes are to be formed in one unit, and integrating six units causes a total of 24 through holes (groups of through holes 3-1 and 4-1) to be formed and aligned lengthwise and crosswise. The through holes 3-1, which exist deeply and on the near side in the direction perpendicular to the space in FIG. 11, are not shown in the figure.

It is noted that the through holes 3-1 and 4-1 to be formed in the packing member 44 in a penetrating manner are not necessarily formed separately, and the through holes 3-1 may be combined with the respective through holes 4-1. This cannot cause, for example, falling solution and rising gas to be intermingled with each other, and since the gas passes through the falling solution to be discharged through a through hole 4-2 above, there is no interference with the function of reducing pressure increase in the wells. In FIG. 12 is shown the structure of thus arranged packing member 44. Also, for that purpose, if the lower end portions of through holes 3-2 and 4-2 to be formed in the cover block body 33 are cut off by a small length to form small blank spaces therein, it is possible to retain the function of reducing pressure increase and pressure reduction further reliably (refer to the two left and right small blank spaces directly below the through holes 3-2 and 4-2 in FIG. 12).

When the cover block body 33 is attached to the bottom support body 31, the lower surface of the bottom part 33a of the cover block body 33 is brought into contact with the upper surface of the packing member 44 and presses the surface. Therefore, the substrate 7 is consequently to be pressed by the cover block body 33 through the packing member 44 to be fixed onto the glass substrate 8.

In one part nearer the peripheral edge of the bottom part 33a of the cover block body 33, there is formed a relatively large-diameter through hole 33d in a vertically penetrating manner through which mixture in the chamber 30 is adapted to go in and out of the central recessed portion 33c. Also, in the central part of the bottom part 33a, there are formed the same number of through holes 3-2 and 4-2 that communicate, respectively, with the through holes 3-1 and 4-1 formed in the packing member 44 in a penetrating manner as the total number of the through holes 3-1 and 4-1 in a vertically penetrating manner. Among these groups of through holes formed in the central part of the bottom part 33a, six units of the through holes 4-2 belonging to the well 2A side, that is, six aligned through holes 4-2 belonging to the well 2A side correspond one-on-one to the six through holes 34c in the guide block body 34 that is attached to the cover block body 33 in the posture as shown in FIG. 8 to share the centerline thereof.

Figure 8:
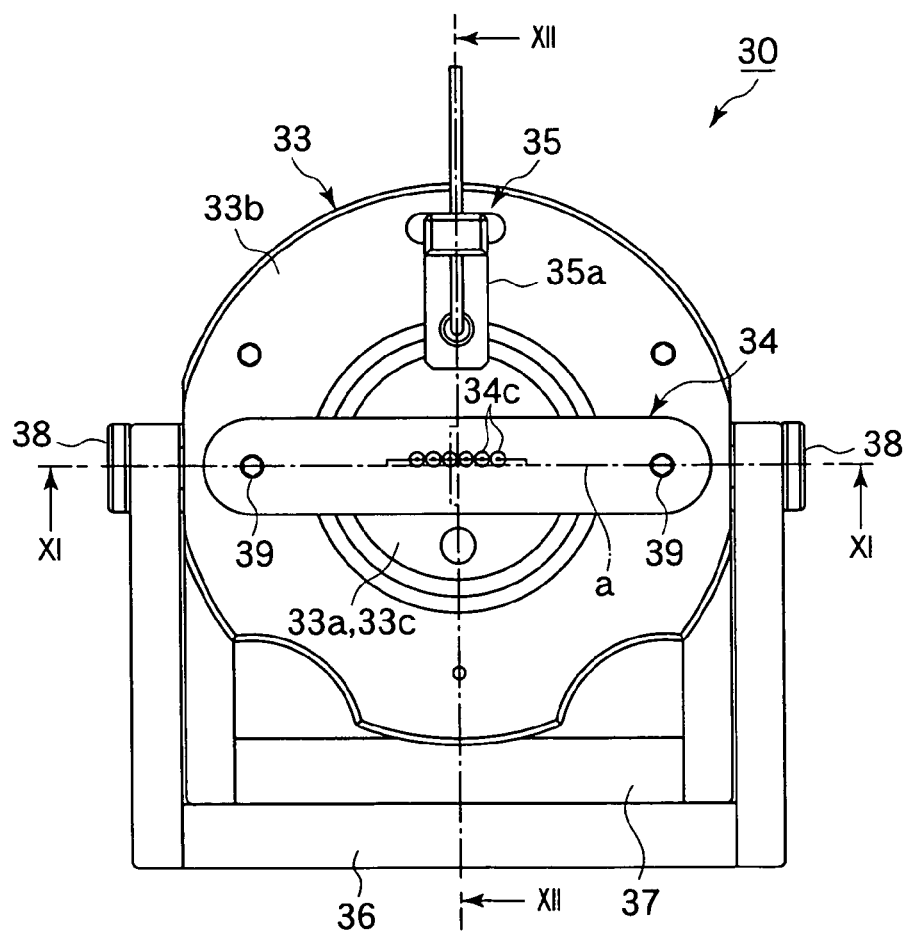
FIG. 8 is a top plan view of the cell observation chamber of FIG. 1.
Figure 9:
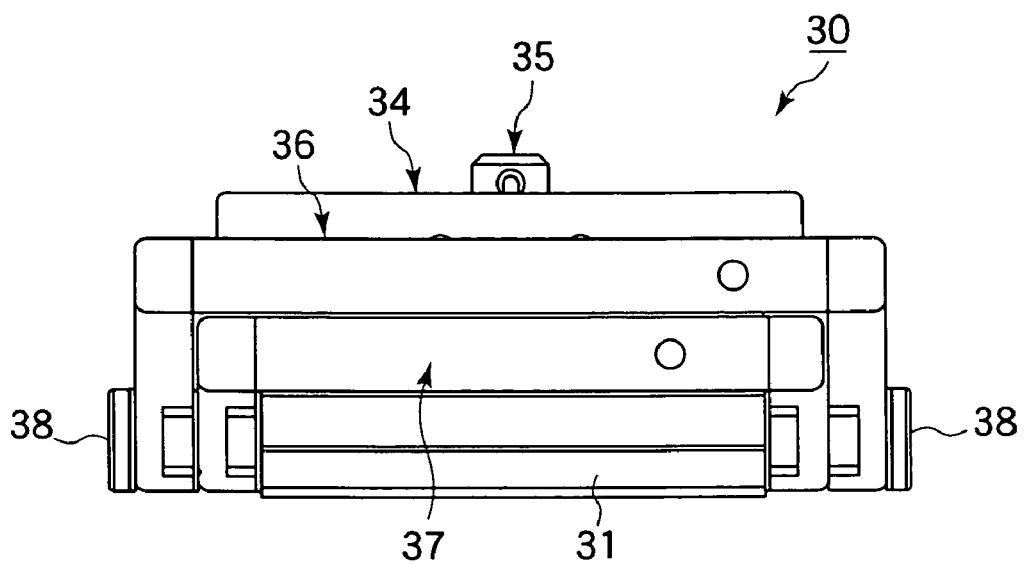
FIG. 9 is a front elevational view of the cell observation chamber of FIG. 1.
Figure 10:
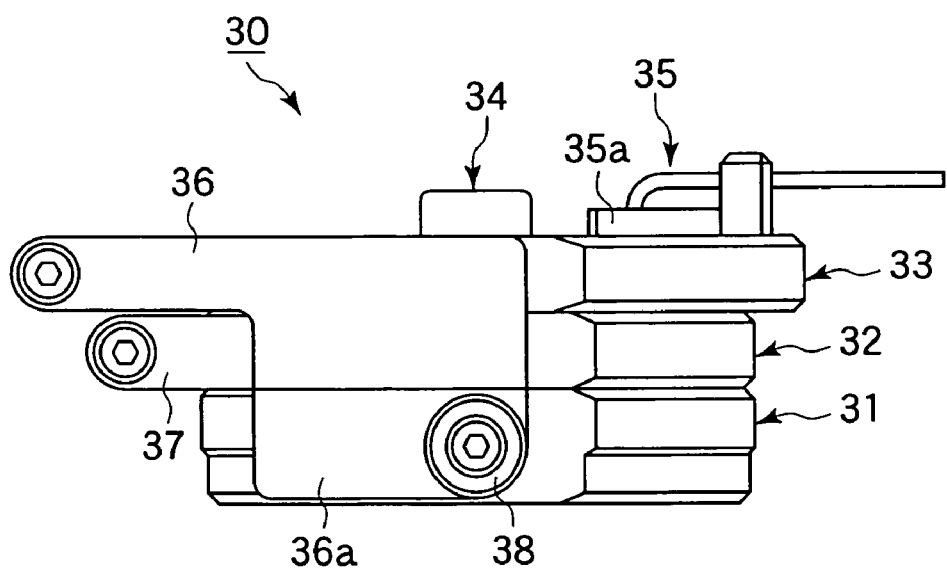
FIG. 10 is a side elevational view of the cell observation chamber of FIG. 1.

When the guide block body 34 is rotated by 180 degrees from the posture as shown in FIG. 8 to switch the positions of the arm parts 34b and 34b on either side with each other, six aligned through holes 4-2 belonging to the well 2B side then correspond one-on-one to the six through holes 34c in the guide block body 34. Thus switching the posture of the guide block body 34 can be employed when the injection of the cell suspension into the well 2A using a micropipette is followed by the injection of the chemotactic factor containing solution into the well 2B using a micropipette.

As is clear from the description above, the through holes 3' and 4' formed in the substrate 7 in a penetrating manner, the through holes 3-1 and 4-1 formed in the packing member 44 in a penetrating manner, and the through holes 3-2 and 4-2 formed in the bottom part 33a of the cover block body 33 in a penetrating manner are communicated with each other, and six units of through hole assemblies that are formed by the through holes 4', 4-1, and 4-2 thus communicating with each other correspond one-on-one to the six through holes 34c formed in the guide block body 34 that is attached to the cover block body 33 in the posture as shown in FIG. 8 to share the centerline thereof (refer to FIGS. 11 and 12). It is noted that the through holes 3' and 4' formed in the substrate 7 in a penetrating manner, which have very small sizes, are not shown in FIGS. 11 and 12. The through hole assemblies composed of the through holes 4-1 and 4-2 correspond to the through holes 4 in FIG. 1.

Accordingly, assuming here that the wells 2A and 2B and the flow path 1 are filled with cell isotonic solution and that the well 2B is provided with chemotactic factor containing solution, when trying to inject cell suspension into the well 2A using a micropipette, after the needlepoint of the micropipette is inserted into one of the through holes 34c that communicates with the well 2A in a unit to be used and is carried while being guided by the hole until reaching a required depth to discharge the cell suspension there, the discharged cell suspension then falls down through the through holes 4-2, 4-1, and 4' in this order to reach the well 2A. In this case, the pressure increase in the well 2A can be released outside through the through holes 3', 3-1, and 3-2, which can minimize the impact of pressure fluctuation on the chemotaxis of cells that are to react with the chemotactic factor containing solution.

The same procedure applies also when trying to inject the chemotactic factor containing solution into the well 2B using a micropipette, and in this case, the chemotactic factor containing solution discharged from the micropipette can fall down through the through holes 4-2, 4-1, and 4' belonging to the well 2B side in this order to reach the well 2B.

Cells in the cell suspension provided to the well 2A move from the well 2A to 2B through the flow path 1 after reacting with the chemotactic factor containing solution in the well 2B. It is possible to observe the state and measure the number of cells at the cell level through the window 31c using the microscope.

In order to thus perform the operation of, for example, detecting the chemotaxis of the cells that move from the well 2A to 2B through the flow path 1 and isolating the cells utilizing the characteristics thereof, it is necessary to control the temperature of the mixture filing these sections so as to be suitable for the activity of the cells. Also when it is demanded that the reaction of the cells due to temperature change be measured and analyzed more precisely, it is necessary to control the temperature of the mixture. It is noted that the mixture filling these sections here means the mixture of the cell isotonic solution and the cell suspension and the mixture of the cell isotonic solution and the chemotactic factor containing solution, where the both mixture has approximately the same temperature.

Figure 15:
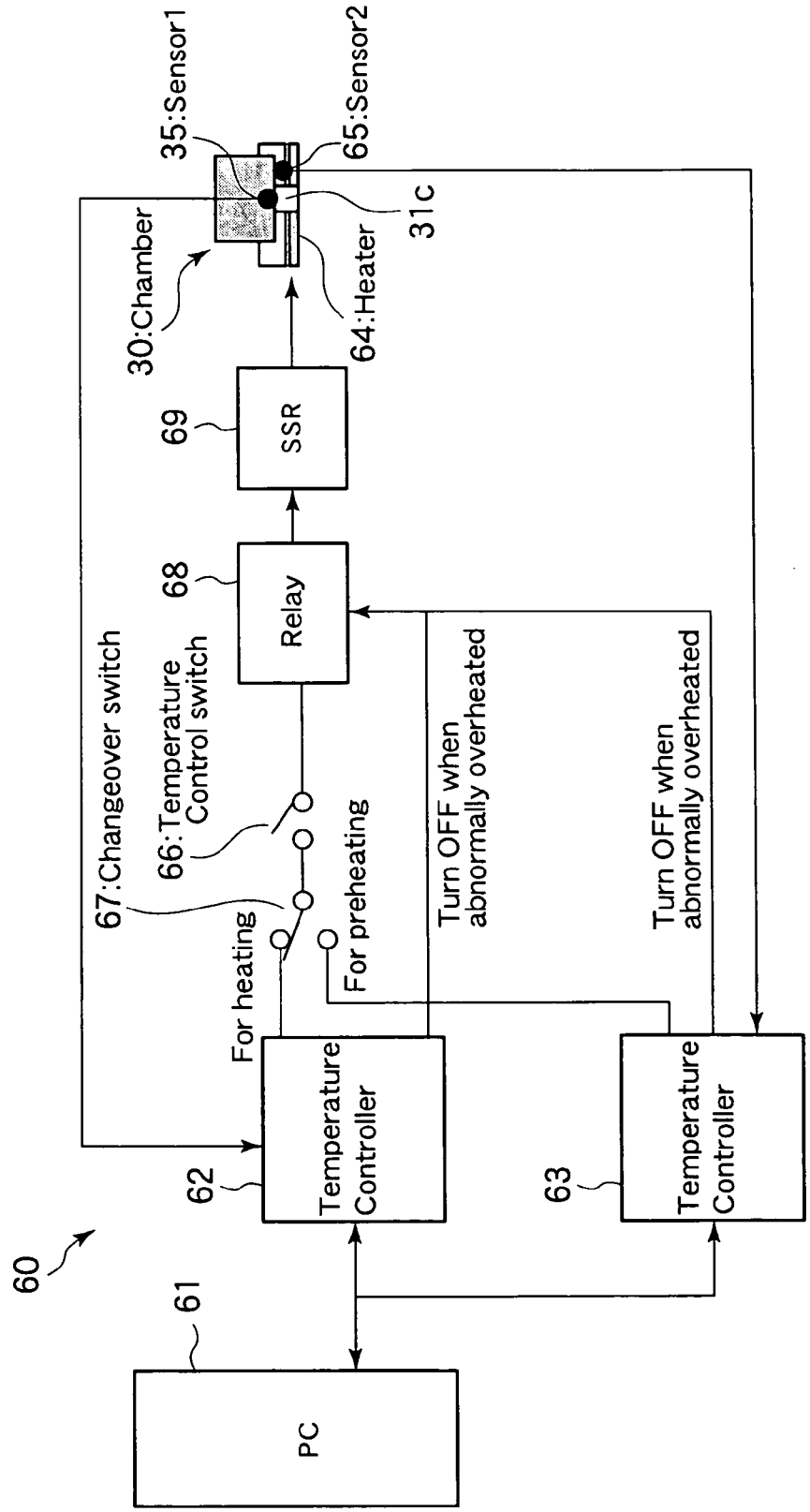
FIG. 15 is a block diagram of a temperature control system for the cell observation chamber of FIG. 1.

For the foregoing purpose, the present embodiment employs two temperature controllers 62 and 63 as shown in FIG. 15, where the first temperature controller 62 is adapted to use the temperature sensor 35 to measure the temperature of the mixture directly and to control the temperature of a heating section 64 to be heated by a heater with the chamber 30 being set thereon to increase the accuracy of the temperature control. Also, the second temperature controller 63 is adapted to heat the heating section 64 preliminarily so that the time required to control the temperature of the mixture to be a required temperature can be shortened. The temperature controller 63 also has a function of preventing the heating section 64 from being overheated.

In order to measure the temperature of the mixture directly using the temperature sensor 35, a temperature sensing part 35b of the temperature sensor 35 extends downward from the pedestal part 35a, as shown in FIG. 12, to be directly sunk into a liquid storage chamber 45 filled with solution equivalent to the mixture. The solution in the liquid storage chamber 45 can receive the indirect heating by the heating section 64 equally with the solutions filling the pair of wells 2A and 2B and the flow path 1 to increase the temperature to be the same as that of the solutions, whereby the temperature sensor 35 can measure approximately the same temperature as that of the solutions filing the pair of wells 2A and 2B and the flow path 1. The liquid level of the solution in the liquid storage chamber 45 is approximately the same as the liquid level L of the mixture in the cover block body 33.

The liquid storage chamber 45 is formed with a recessed portion formed by partially and vertically chipping the outer peripheral wall of the body part of the cover block body 33 being surrounded by the inner peripheral wall of the intermediate support body 32. It is preferable that the liquid storage chamber 45 be provided separately from the wells 2A and 2B, the flow path 1, and the sections communicating with these portions. For this reason, it is arranged that there is interposed a packing (not shown in the figures) at the lower part of the liquid storage chamber 45 where the liquid storage chamber 45 is connected to the wells 2A and 2B, the flow path 1, and the sections communicating with these portions. This allows the temperature sensing part 35b of the first temperature controller 62 to measure the temperature of the solutions containing cells and filling the pair of wells 2A and 2B and the flow path 1 precisely without contaminating the solutions.

To describe the in-chamber mixture temperature control system 60 in more detail with reference to the block diagram shown in FIG. 15, when a temperature control switch 66 is first turned ON and a changeover switch 67 is turned ON for preheating, a preheating operation for the heating section 64 is started under the control of the temperature controller 63. The preheating operation is to be performed while measuring the temperature of the heating section 64 using a sensor 65 and feeding back the measured value. The preheating temperature is to be specified by a computer 61. The computer 61 is incorporated in the laptop computer 50. The numeral 69 indicates a solid-state relay (SSR).

When the temperature of the heating section 64 reaches a predetermined preheating temperature and the cell observation chamber 30 is placed on the heating section 64, the changeover switch 67 is turned ON for heating to start a heating operation for the heating section 64 under the control of the temperature controller 62. This heating operation, which is aiming at heating the mixture in the chamber to be a predetermined temperature, is to be performed while measuring the temperature of the mixture in the chamber using the sensor 35 and feeding back the measured value. The heating temperature is to be specified by the computer 61. Since the heating section 64 has been heated to be the predetermined temperature through the foregoing preheating operation, this heating operation can heat the mixture in the chamber to be the predetermined temperature in a short time.

When the temperature of the mixture in the chamber reaches the predetermined temperature, the temperature controller 62 performs heating control for the heating section 64 to keep the temperature. If the temperature of the heating section 64 increases abnormally (e.g. 43° C.) for some reasons, for example, that the chamber 30 is not in contact with the heating section 64, the temperature controller 63 operates the relay 68 to shut off the circuit. It is noted that the temperature controller 62 is also adapted to operate the relay 68 to shut off the circuit if the temperature of the mixture in the chamber increases abnormally (e.g. 38 to 40° C.).

The computer 61 is adapted to monitor and display the temperature of the heating section 64 and the mixture in the chamber, the state of the sensors 35 and 65, etc. constantly, and to specify a heating temperature and a preheating temperature, respectively, for the temperature controllers 62 and 63.

Here will be described in detail an actual procedure for assembling the cell observation chamber 30 according to the present embodiment.

The glass substrate 8 is first attached to the bottom support body 31. Then, the intermediate support body 32 is fitted into the bottom support body 31, and the cam control lever 37 is rotated to bring the intermediate support body 32 into pressurized contact with the bottom support body 31 from above through the O-ring 43 and to attach the intermediate support body 32 to the bottom support body 31. This can prevent medium from leaking to give the assembly composed of these components a function as a container. Next, the substrate 7 is placed on the glass substrate 8 while being guided by the opening portion 32c formed in the central part of the bottom part 32a of the intermediate support body 32, and the cover block body 33 with the packing member 44 attached to the bottom surface thereof is fitted into the intermediate support body 32, and then the cam control lever 36 is rotated to bring the packing member 44 into pressurized contact with the substrate 7 from above and to bring the substrate 7 into pressurized contact with the glass substrate 8. At the same time, the cover block body 33 is brought into pressurized contact with the intermediate support body 32 through the O-ring 42 so that it is possible to prevent the medium from leaking to give the general assembly (cell observation chamber 30) composed of these components also a function as a container.

The cell observation chamber 30 according to the present embodiment, which is thus arranged, can exhibit the following effects.

The attachment of the intermediate support body 32 to the bottom support body 31 and of the cover block body 33 to the bottom support body 31 is achieved by bringing the respective contact surfaces into vertically pressurized contact with each other using the lever mechanisms (cam control levers) 36 and 37 with the cam mechanism incorporated therein, which eliminates the need for a specialized tool for assembling and disassembling, whereby it is possible to improve the operationality in assembling and disassembling dramatically. This also makes it possible to keep a constant pressure at any time to bring the components (bottom support body 31, intermediate support body 32, and cover block body 33) associated with the attachment into pressurized contact with each other, whereby it is possible to prevent the solutions in the chamber from leaking reliably.

Further, it is arranged that the cam mechanism comprises: the cam grooves 36b and 37b formed, respectively, in the both leg parts of the two U-shaped levers 36 and 37 that are supported rotatably by the bottom support body 31; and the pins 40 and 41 implanted, respectively, at two corresponding points on the outer peripheral surface of the cover block body 33 and the intermediate support body 32, the pins being adapted to move within the cam grooves 36b and 37b in a sliding manner. This allows the structure of the cam mechanism to be simplified significantly, and the attachment/detachment of the intermediate support body 32 to/from the bottom support body 31 and of the cover block body 33 to/from the intermediate support body 32 can be achieved only by rotating the respective U-shaped levers 36 and 37, which facilitates the operation of the cam mechanism significantly.

In addition, the guide block body 34 is further attached to the cover block body 33, in the guide block body 34 being formed a plurality of through holes 34c for guiding the micropipette that has inhaled either the cell suspension or the chemotactic factor containing solutions therethrough in a vertically penetrating manner. This facilitates significantly the operation of injecting or removing the cell suspension and the chemotactic factor containing solution into/from the wells in the cell observation chamber 30 using the micropipette.

It is possible to additionally exhibit various kinds of such effects as mentioned above.

It is noted that the present invention is not restricted to the above-described embodiment, and various modifications may be made without departing from the gist thereof.

For example, instead of lever mechanisms, such as the cam control levers 36 and 37, with a cam mechanism incorporated therein, it is possible to employ a clamp mechanism based on a toggle clamp system or a compression clamp system in which a nail is adapted to clamp after compression.

What is claimed is:

1. A cell observation chamber for use in an apparatus for detecting cell chemotaxis and for isolating chemotactic cells, said chamber comprising:
    a dish-shaped bottom support body with a window for observing the movement of cells provided in the center of a bottom surface thereof;
    a glass substrate adapted to be placed on the bottom surface of said bottom support body;
    a dish-shaped intermediate support body with an opening in the center of a bottom part thereof, said intermediate support body being adapted to be attached to said bottom support body to press and fix said glass substrate from above onto the bottom surface of said bottom support body;
    a substrate having, in a surface facing said glass substrate, at least a pair of wells and a flow path providing communication between said wells, said substrate further having a plurality of through holes for guiding cell suspension and chemotactic factor containing solution therethrough and into said wells, said substrate being adapted to be fixed onto the surface in the central part of said glass substrate;
    a packing member with a plurality of through holes for guiding said cell suspension and said chemotactic factor containing solution therethrough formed therein, said packing member being adapted to be fitted into said opening in the center of the bottom part of said intermediate support body to press said substrate from above; and
    a dish-shaped cover block body with a plurality of through holes for guiding said cell suspension and said chemotactic factor containing solution therethrough formed in the center of a bottom thereof, said cover block body being adapted to be attached to said bottom support body with said intermediate support body attached thereto to press and fix said substrate from above onto said glass substrate through said packing member;
    a first cam mechanism comprising a pair of pins symmetrically arranged on and extending from a periphery of said cover block body and a first U-shaped cam lever pivotally mounted on said bottom support body and including a first handle and a first pair of legs respectively fixed to opposing ends of the handle, each of said first legs having a cam groove receiving one of the pins extending from said cover block body, whereby movement of said first cam lever from a first position to a second position forces together said cover block body and said bottom support body, with said intermediate support body clamped therebetween; and
    a second cam mechanism comprising a pair of pins symmetrically arranged on and extending from a periphery of said intermediate support body and a second U-shaped cam lever pivotally mounted on said bottom support body and including a second handle and a second pair of legs respectively fixed to opposing ends of the second handle, each of said second legs having a cam groove receiving one of the pins extending from said intermediate support body, whereby movement of said second cam lever from a first position to a second position forces together the intermediate support body and said bottom support body.

2. The cell observation chamber according to claim 1, further comprising:
    a guide block body attached to said cover block body, said guide block body having a plurality of through holes for guiding a micropipette to dispense either said cell suspension or said chemotactic factor containing solution therethrough into one of said wells.

3. The cell observation chamber according to claim 1, further comprising:
    a pair of support shaft portions symmetrically arranged on and extending from said bottom support body; and
    wherein said legs of said first and second cam levers are mounted on said. support shaft portions.

4. The cell observation chamber according to claim 1, wherein:
    said cover block body and said intermediate support body each have a peripheral flange; and said bottom support body has a rim presenting an annular surface; and further comprising:
    first holes in a surface of the peripheral flange of the cover block body and second holes aligned with the first holes and formed in a surface of the peripheral flange of the intermediate support body facing the flange of the cover block body and a first pin received in each of said second holes and in a first hole aligned therewith for circumferentially positioning said cover block body on said intermediate support body; and
    third holes in another surface of the peripheral flange of the intermediate support body facing the bottom support body and fourth holes aligned with the third holes and formed in the annular surface of said bottom support body and a second pin received in each of said third holes and in a fourth hole aligned therewith for circumferentially positioning said intermediate support body on said bottom support body.

5. The cell observation chamber according to claim 4, wherein said first pins have different diameters and said second pins have different diameters.

* * * * *